United States Patent [19]

Yamanaka et al.

[11] 4,288,642

[45] Sep. 8, 1981

[54] PRODUCTION OF ω-ALKENE-1-OLS

[75] Inventors: Tohr Yamanaka, Kamakura; Takashi Imai, Hiratsuka, both of Japan

[73] Assignee: Takasago Perfumery Co., Ltd., Tokyo, Japan

[21] Appl. No.: 114,529

[22] Filed: Jan. 23, 1980

[30] Foreign Application Priority Data

Jan. 23, 1979 [JP] Japan .................................. 54-6696

[51] Int. Cl.$^3$ ............................................. C07C 29/60
[52] U.S. Cl. ................................ 568/903; 252/522 R; 568/876; 260/410.6
[58] Field of Search ............................... 568/903, 876

[56] References Cited

U.S. PATENT DOCUMENTS

| | | | |
|---|---|---|---|
| 1,942,812 | 6/1934 | Guenther et al. | 568/903 |
| 2,137,667 | 11/1938 | Eipper | 260/410.6 |
| 2,415,378 | 2/1947 | Vaughn | 568/876 |
| 2,454,936 | 11/1948 | Morey | 568/903 |
| 3,001,975 | 9/1961 | Beavers et al. | 568/903 |
| 3,329,713 | 7/1967 | Hoyle et al. | 568/876 |
| 3,329,826 | 7/1967 | Pine et al. | 260/410.6 |
| 3,332,983 | 7/1967 | Barie et al. | 260/410.6 |

*Primary Examiner*—Joseph E. Evans
*Attorney, Agent, or Firm*—Sughrue, Mion, Zinn, Macpeak and Seas

[57] ABSTRACT

A process for producing ω-alkene-1-ols which comprises reacting an α,ω-alkanediol having 4 to 14 carbon atoms with a fatty acid selected from the group consisting of stearic acid, palmitic acid and a mixture of stearic acid and palmitic acid.

4 Claims, No Drawings

PRODUCTION OF ω-ALKENE-1-OLS

BACKGROUND OF THE INVENTION

1. Field of the Invention

The present invention relates to a novel process for producing ω-alkene-1-ols.

2. Description of the Prior Art

Heretofore, a process for producing olefins by dehydrating primary alcohols having one hydroxyl group using an acidic or basic material as the catalyst has been known. However, this dehydration reaction is often accompanied by ether formation due to intermolecular dehydration, and by double bond transfer in the dehydrated products (Eugen Müller, Methoden der Organischen Chemie, Bd V/lb, 45 (1972)). Moreover, when this process is applied to α,ω-alkanediols having two hydroxyl groups, large amounts of various diolefins, various alkene-1-ols and polyethers are formed, which not only gives a far smaller yield of the desired product, ω-alkene-1-ol, but also makes it extremely difficult to isolate and purify the ω-alkene-1-ol from the resulting reaction mixture by conventional distillation.

A process for producing olefins by thermally decomposing acetates of primary alcohols (ibid, Bd V/lb, 105 (1972)) has also been known. In this process, although double bond transfer does not take place, the process requires two steps because the acetates must be prepared beforehand and separated prior to thermal decomposition and thus is complicated. In addition, in the production of ω-alkene-1-ols using this process, another disadvantage is that when the starting material, monoacetate of an α,ω-alkanediol, is produced it is difficult to obtain alone at a good yield because the α,ω-diacetate is produced as a by-product. Further, the acetic acid produced by the thermal decomposition undergoes decomposition to make its recovery difficult. Therefore, this process is not suitable for commercial purposes.

On the other hand, it is known that the direct dehydration of alkane-1,4-diols produces tetrahydrofuran derivatives by the intramolecular dehydration (Journal of Organic Chemistry, Vol. 32, 3650 (1967)).

SUMMARY OF THE INVENTION

Studies have been directed to overcome the above drawbacks of prior art processes and it has been found that when an α,ω-alkanediol is heated together with a higher fatty acid having a high boiling point, only one of the hydroxyl groups of the α,ω-alkanediol reacts with the fatty acid to produce the monoester, which then undergoes further thermal decomposition to give an ω-alkene-1-ol and liberate the original fatty acid.

Accordingly, the present invention is a process for producing ω-alkene-1-ols which comprises heating an α,ω-alkanediol having 4 to 14 carbon atoms together with stearic acid, palmitic acid or a mixture of stearic acid and palmitic acid.

DESCRIPTION OF THE INVENTION

The process of the present invention can be advantageously carried out in a continuous manner described below because the stearic acid and palmitic acid liberated by the thermal decomposition can be used directly as the starting materials in the subsequent reaction, although this process can also be conducted batchwise.

Using a distillation apparatus equipped with a distillation column which is adapted for fractional distillation, the higher fatty acid and α,ω-alkanediol are charged at a molar ratio of about 1:0.8 to 1:3.0 and heated to reflux. The distillation is started when the temperature at the column top is about intermediate the boiling points of the α,ω-alkanediol and the ω-alkene-1-ol. The distillate chiefly consists of a mixture of water, the ω-alkene-1-ol and the unreacted α,ω-alkanediol. The reaction is continued by continuously feeding the α,ω-alkanediol in an amount equal to that of the distillate while maintaining the necessary temperature in the reactor. The reaction temperature is preferably in a range of 310° to 360° C. so that the esterification of the α,ω-alkanediol and the higher fatty acid and the decomposition of the resulting ester are brought about. The temperature can be maintained in the above range by selecting the proportion of the α,ω-alkanediol and the fatty acid used and the degree of vacuum in the reaction system depending on their natures. In this connection, since boiling points of the starting materials, α,ω-alkanediols at normal pressure are up to 350° C. except 1,14-tetradecanediol, it is not necessary to bring the system in the distillation column to reduced pressure but it is preferred to make the pressure in the distillation column 200 to 700 mm Hg in order to improve the yield of the ω-alkene-1-ols when using α,ω-alkanediols having 10 or more carbon atoms. With α,ω-alkanediols having up to 6 carbon atoms, the temperature can be kept at about 310° to 360° C. by establishing the molar ratio of the α,ω-alkanediol to the higher fatty acid at about 1:1 to 0.8:1 in the reactor.

As the higher fatty acid, stearic acid or palmitic may be used alone or in combination with each other. Since these higher fatty acids supplied as the initial feeding enable the continuous reaction for 20 days or more, it is possible to produce the ω-alkene-1-ol in an amount of 10 to 200 times that of the fatty acid used.

If the number of the theoretical plates of the distillation column is 3 to 5, the content of the ω-alkene-1-ol in the distillate can be 70% by weight or higher.

As described above, in accordance with the present invention, ω-alkene-1-ols can be very advantageously produced from α,ω-alkanediols on a commercial scale. The ω-alkene-1-ols which are produced according to the present invention are useful themselves and can also be used as starting materials for the syntheses of various compounds, particularly, 9-decene-1-ol and 5-hexene-1-ol which possess the aromas of rose and fresh verdure, respectively, thus making them useful as fragrances, and 13-tetradecene-1-ol which is important as an intermediate for the synthesis of pentadecanolite.

The present invention is more particularly described in the following examples.

EXAMPLE 1

55.2 g of a stearic acid and palmitic acid (44:56 in weight) mixture and 61.5 g of 1,10-decanediol were placed in a 200 cc flask equipped with a Vigreux distillation column (20 mmφ×200 mm), a reflux condenser and a heating mantle (150 W) and heated to reflux at 330° to 350° C. The pressure within the apparatus was maintained at 700 mm Hg as measured at the top of the column using a suction pump. The temperature at the top of the column showed 295° C. initially and gradually dropped. When the temperature reached 265° to 270° C., the collection of the distillate was started by distilling at a rate of 10 g per hour and concurrently feeding 10 g per hour of 1,10-decanediol to the flask to carry out a continuous reaction for 150 hours. As a result, 1498 g of the distillate were obtained from 1500 g of 1,10-decanediol. After removal of 126 g of water produced from the distillate, the residual oil was analyzed by gas chromatography and it was found to contain 71.7 wt% 9-decene-1-ol, 20.1 wt% 1,10-decanediol, 1.2 wt% decadienes, and 6.9 wt% by-produced decene-1-ols. The oil amounting to 1372 g was then fractionated using a 30-plate Heli-pak (a product from Podbielniak, Inc.) packed column to obtain 885 g of the desired product, 9-decene-1-ol, as the distillate at 74° C./1 mm Hg; 270 g of the unreacted 1,10-decanediol; 16 g of the by-produced decadienes and 201 g of the by-produced decene-1-ols. The identification of the desired product, 9-decene-1-ol, was established by the following analytical results.

MS (m/e): 156 (M+);
IR (cm$^{-1}$, neat): 3070, 1643, 995 and 910;
NMR (δ, ppm, 20% in CCl$_4$ solution): 4.74–6.04

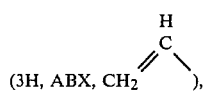

3.45 (2H, t, J=6 cps, —CH$_2$—CH$_2$—OH), 2.02 (2H, t, d, J=6 cps,

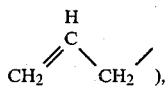

1.28 (12H, b. s., —(CH$_2$)$_n$—) and 4.23 (1H, s, —CH$_2$OH).

EXAMPLE 2

Using a similar apparatus to that of Example 1, 55.2 g of palmitic acid and 20 g of 1,6-hexanediol were added to the flask and the liquid temperature in the flask was raised to 330° to 350° C. at normal pressure to reflux. The distillation was effected at a rate of 10 g per hour over a temperature range of 204° to 215° C. as measured at the top of the column. Concurrently with the distillation, 10 g per hour of 1,6-hexanediol were added to the flask and reacted continuously for 24 hours. As a result, 238 g of the distillate were obtained from 240 g of 1,6-hexanediol. After removal of 31.9 g of water produced from the distillate, the residual oil amounting to 206 g was fractionated using a 30-plate Heli-pak packed column to obtain 140 g of the desired product, 5-hexene-1-ol, as the distillate at 74° C./28 mm Hg, 31 g of the unreacted 1,6-hexanediol, 5.5 g of the by-produced hexadienes and 29.5 g of the distillation residue. The identification of the desired product, 5-hexene-1-ol, was confirmed by the following analytical results.

MS (m/e): 100 (M+);
IR (cm$^{-1}$, neat): 3070, 1643, 995 and 910;
NMR (δ, ppm, 20% in CCl$_4$ solution): 4.75–6.07

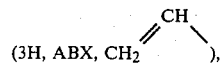

3.48 (2H, t, J=7, cps, —CH$_2$—CH$_2$-OH), 2.05 (2H, t, d, J=7 cps,

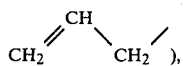

1.48 (4H, m, —CH$_2$—CH$_2$—) and 3.58 (1H, s, —CH$_2$-OH).

EXAMPLE 3

Using a similar apparatus to that of Example 1, 102.5 g of palmitic acid and 43.2 g of 1,4-butanediol were added to the flask and the liquid temperature in the flask was raised to 330° to 345° C. at normal pressure to reflux. The distillation was effected at a rate of 10 g per hour over a temperature range of 140° to 170° C. as measured at the top of the column. Concurrently with the distillation, 10 g per hour of 1,4-butanediol were added to the flask and reacted continuously for 32 hours. As a result, 290.1 g of the distillate were obtained from 323 g of 1,4-butanediol. The distillate forming a two layered liquid system was transferred to a Claisen flask without separation and distilled at a boiling point of 102° C. at normal pressure to seperate into 174.5 g of the distillate and 115.5 g of the distillation residue. The thus obtained distillate formed two layers of aqueous and oil phases and it was found that the aqueous phase consisted of a mixture of water and tetrahydrofuran (37.4 g and 25.8 g, respectively) and the oil phase consisted of a mixture of butadiene dimer and 3-butene-1-ol (10.7 g and 100.6 g, respectively). The oil phase was fractionated using an 80 cm Heli-pak packed column to obtain 98 g of the desired product, 3-butene-1-ol at 74° C./28 mm Hg. The identification of the desired product, 3-butene-1-ol, was confirmed by the following analytical results.

MS (m/e): 72 (M+);
IR (cm$^{-1}$, neat): 3070, 1643, 990 and 915;
NMR (δ, ppm, 20% in CCl$_4$ solution): 4.85–6.09

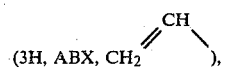

3.56 (2H, t, J=6 cps, —CH$_2$-CH$_2$—OH), 2.44 (2H, t, d, J=6 cps,

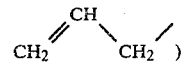

and 3.29 (1H, s, —CH$_2$OH).

EXAMPLE 4

Using a similar apparatus to that of Example 1, 55.3 g of stearic acid and 84.2 g of 1,14-tetradecanediol were added to the flask, the liquid temperature was raised to 330° to 340° C. while maintaining the system under vacuum of 260 mm Hg and reflux was conducted. When the temperature at the top of the column reached 235° to 240° C., the distillation was started at a rate of 10 g per hour and the reaction was carried out continuously for 19 hours while supplying 10 g per hour of 1,14-tetradecanediol to the flask concurrently. As a result, 187 g of the distillate were obtained from 190 g of 1,14-tetradecanediol. After separating 7.7 g water produced from the distillate, 179.3 g of the oil were fractionated using an 80 cm Heli-pak packed column to obtain 59 g of the desired 13-tetradecene-1-ol, as the distillate at 120° to 122° C./2.5 mm Hg, 84 g of the unreacted 1,14-tetradecanediol and 36.3 g of the by-produced tetradecadienes. The identification of the desired product, 13-tetradecene-1-ol, was confirmed by the following analytical results.

IR (cm$^{-1}$, neat): 3060, 1643, 995 and 910;
NMR (δ, ppm, 20% in CCl$_4$ solution): 4.74–6.05

(3H, ABX, 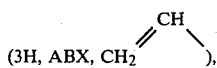), 3.46 (2H, t, J=6 cps, —CH$_2$—C$\underline{H}_2$OH), 2.01 (2H, t, d, J=6 cps,

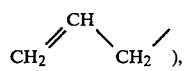), 1.27 (20H, b.s., —(CH$_2$)$_n$—) and 4.13 (1H, s, —CH$_2$O$\underline{H}$).

While the invention has been described in detail and with reference to specific embodiments thereof, it will be apparent to one skilled in the art that various changes and modifications can be made therein without departing from the spirit and scope thereof.

What is claimed is:

1. A process for producing an ω-alkene-1-ol which comprises heating an α,ω-alkanediol having 4 to 14 carbon atoms together with a fatty acid selected from the group consisting of stearic acid, palmitic acid and a mixture thereof, the molar ratio of said fatty acid to said α,ω-alkanediol being about 1:0.8 to 1:3.0, at a temperature of about 310° to 360° C. in the absence of a catalyst, and continuously feeding the α,ω-alkanediol to the reaction system, with the pressure of the reaction system being controlled to 200 to 700 mmHg, while maintaining the same temperature and simultaneously distilling the ω-alkene-1-ol.

2. The process of claim 1, wherein said fatty acid is stearic acid.

3. The process of claim 1, wherein fatty acid is palmitic acid.

4. The process of claim 1, wherein said ω-alkene1-ol is 3-butene-1-ol, 5-hexene-1-ol, 9-decene-1-ol or 13-tetradecene-1-ol.

* * * * *